(12) United States Patent
Snell et al.

(10) Patent No.: US 8,592,730 B2
(45) Date of Patent: Nov. 26, 2013

(54) HEATER ASSEMBLY FOR SUTURE WELDER

(75) Inventors: Douglas Snell, Amesbury, MA (US);
Francis P. Harrington, Peabody, MA (US); Paul Westhaver, Dartmouth (CA);
Tom David Marro, Magnolia, MA (US);
Paul Schmitt, North Andover, MA (US)

(73) Assignee: Tornier, Inc., Bloomington, MN (US)

( * ) Notice: Subject to any disclaimer, the term of this patent is extended or adjusted under 35 U.S.C. 154(b) by 1256 days.

(21) Appl. No.: 11/959,882

(22) Filed: Dec. 19, 2007

(65) Prior Publication Data
US 2008/0210683 A1 Sep. 4, 2008

Related U.S. Application Data

(60) Provisional application No. 60/876,458, filed on Dec. 20, 2006, provisional application No. 60/876,196, filed on Dec. 20, 2006.

(51) Int. Cl.
*H05B 1/02* (2006.01)
(52) U.S. Cl.
USPC ........... 219/497; 219/494; 219/505; 219/541; 219/543; 219/546
(58) Field of Classification Search
CPC ........................................... H05B 1/02
USPC ......... 219/494, 497, 501, 504, 505, 541, 546, 219/543
See application file for complete search history.

(56) References Cited

U.S. PATENT DOCUMENTS

| 2,961,522 | A | * | 11/1960 | Hammer | 219/541 |
| 3,934,119 | A | * | 1/1976 | Trenkler | 219/543 |
| 4,423,401 | A | | 12/1983 | Mueller | |
| 4,501,951 | A | | 2/1985 | Benin et al. | |
| 4,656,339 | A | | 4/1987 | Grise | |
| 5,062,146 | A | * | 10/1991 | Kagechika | 392/432 |
| 5,408,577 | A | | 4/1995 | Weber, Jr. et al. | |

(Continued)

FOREIGN PATENT DOCUMENTS

| WO | 2008079247 | 7/2008 |
| WO | 2008079248 | 7/2008 |

OTHER PUBLICATIONS

PCT International Search Report—(PCT/US07/25978) Date of Mailing Jun. 24, 2008.

(Continued)

*Primary Examiner* — Mark Paschall
(74) *Attorney, Agent, or Firm* — Knobbe Martens Olson & Bear, LLP

(57) ABSTRACT

Disclosed is a heater device for thermally welding suture strands, including: a substrate extending from a first end to a second end along a substrate axis, and having a substantially planar heater support surface; a joinder layer disposed on the heater support surface; a heater element extending from a first end to a second end along a heater axis thereof and disposed on the joinder layer, the heater element being a layer and being coupled to the support surface by the joinder layer; an electrical interface including a first electrically conductive element coupled to the first end of the heater element, and a second electrically conductive element coupled to the second end of the heater element. In some embodiments, the heater element is elongated along the heater axis.

26 Claims, 4 Drawing Sheets

(56) References Cited

U.S. PATENT DOCUMENTS

| | | | |
|---|---|---|---|
| 5,441,507 A | 8/1995 | Wilk | |
| 5,502,293 A * | 3/1996 | Ohnishi et al. | 219/543 |
| 5,649,937 A * | 7/1997 | Bito et al. | 606/139 |
| 5,893,880 A | 4/1999 | Egan et al. | |
| 5,999,085 A | 12/1999 | Szwarc et al. | |
| 6,056,751 A | 5/2000 | Fenton | |
| 6,078,028 A * | 6/2000 | Cooper et al. | 219/270 |
| 6,121,590 A * | 9/2000 | Kobayashi et al. | 219/553 |
| 6,866,672 B2 | 3/2005 | Mollenauer et al. | |
| 6,921,882 B2 * | 7/2005 | Gadow et al. | 219/465.1 |
| 2002/0035371 A1 | 3/2002 | Westhaver et al. | |
| 2002/0115997 A1 | 8/2002 | Truckai et al. | |
| 2002/0116027 A1 | 8/2002 | Egan et al. | |
| 2003/0039299 A1 | 2/2003 | Horovitz et al. | |
| 2004/0037542 A1 | 2/2004 | Kanishi | |
| 2006/0212045 A1 | 9/2006 | Schilling et al. | |
| 2009/0182353 A1 | 7/2009 | Snell et al. | |

OTHER PUBLICATIONS

PCT International Search Report—(PCT/US07/25977) Date of Mailing Aug. 12, 2008.

* cited by examiner

| | $t_1$ | $t_2$ | $t_3$ | $t_4$ | $t_5$ | $t_6$ | ... | $t_{n-1}$ | $t_n$ |
|---|---|---|---|---|---|---|---|---|---|
| HEATER A | ON | OFF | ON | OFF | ON | OFF | ... | ON | OFF |
| HEATER B | OFF | ON | OFF | ON | OFF | ON | ... | OFF | ON |

HEATER ASSEMBLY FOR SUTURE WELDER

CROSS REFERENCE TO RELATED APPLICATION

The present application claims priority from U.S. Provision Application Ser. No. 60/876,458 filed Dec. 20, 2006 and U.S. Provisional Application Ser. No. 60/876,196 filed Dec. 20, 2006, each of which is incorporated by reference herein in its entirety.

BACKGROUND

The present disclosure relates to improvements in sutures and suturing techniques.

In surgical procedures, a suture is typically used to stitch or secure the edges of tissue together to maintain them in proximity until healing is substantially completed. The suture is generally directed through the portions of the tissue to be joined and formed into a single loop or stitch, which is then knotted in order to maintain the wound edges in the appropriate relationship to each other for healing to occur. In this manner, a series of stitches of substantially uniform tension can be made in tissue. Because the stitches are individual and separate, the removal of one stitch does not require removal of them all or cause the remaining stitches to loosen. However, each individual stitch requires an individual knot or some other stitch-closing device for securing the stitch around the wound.

It is sometimes necessary or desirable to close a wound site with sutures without having to form knots or incorporate loop-closing devices in the sutures, such as, for example, in surgical repair of delicate organs or tissues, where the repair site is relatively small or restricted. Apparatuses and methods for fusing suture loops have therefore also been provided. A fused suture loop must provide the appropriate tension on the wound edges and the appropriate strength to maintain the wound edges in sufficient proximity for a sufficient time to allow healing to occur.

Polymer sutures are particularly amenable to various fusing or joining processes, such as, for example, welding, whereby sections of the sutures can be fused together upon application of sufficient heat to the sections to cause partial melting and fusion of the sections. U.S. Pat. No. 5,893,880, for example, discloses a fused loop of an elongated material, such as a surgical suture, and apparatus for making the loop. Portions of one or more segments to be joined together are fused in a welding process to form a welded joint. The shear area of the fused portion of the joint determines the strength of the joint and is thus preferably relatively large. Various configurations for the welding apparatus facilitate the creation of relatively large fused portions of the joint by maximizing contact between at least one of the welding members of the apparatus and at least one of the segments to be joined.

SUMMARY

The present disclosure is directed to a heater device for providing reliable, controlled heat to surgical suture material to create secure suture welds, particularly suited for use in creating secured sutures during endoscopic surgery.

In one aspect, disclosed is a heater device for thermally welding suture strands, including: a substrate extending from a first end to a second end along a substrate axis, and having a substantially planar heater support surface; a joinder layer disposed on the heater support surface; a heater element extending from a first end to a second end along a heater axis thereof and disposed on the joinder layer, the heater element being a layer and being coupled to the support surface by the joinder layer; an electrical interface including a first electrically conductive element coupled to the first end of the heater element, and a second electrically conductive element coupled to the second end of the heater element. In some embodiments, the heater element is elongated along the heater axis. In some embodiments, each of the first and second wires extend from respective ends of the substrate in a direction at least in part orthogonal to said support surface In some embodiments, the substrate is elongated along the substrate axis; and the electrical interface includes a first wire; and a second wire. A first electrically conductive layer is disposed on the substrate and the joinder layer, and electrically coupling the first wire and the first end of the heater element A second electrically conductive layer is disposed on the substrate and the joinder layer, and electrically coupling the second wire and the second end of the heater element.

In some embodiments, the substrate includes: a first open-faced groove in the first end thereof and extending from and at least in part orthogonal to the support layer, and a second open-faced groove in the second end thereof and extending from and at least in part orthogonal to the support layer The first groove and the second groove each include a metal layer disposed at least in part thereon, and where the first wire and the second wire are bonded to a respective one of the metal layers of the first groove and the second groove.

In some embodiments, the heater element layer has a thickness in the range 2000-3000 Angstroms. In some embodiments, the heater element is gold. In some embodiments, the joinder layer has a thickness in the range 300-500 Angstroms. In some embodiments, where the joinder layer is a tungsten alloy. In some embodiments, the metal layers are gold. In some embodiments, the metal layers have a thickness in the range of 900-1100 Angstroms.

In some embodiments, the bonding between the first and second wires to the metal layers of the grooves is solderless. In some embodiments, the bonding is at least in part a thermal compression weld. In some embodiments, the grooves have a partial conical contour and the bonding is at least in part an interference fit.

In some embodiments, the heater element is a resistive temperature device (RTD) having resistivity which varies monotonically with temperature over a predetermined operating temperature range.

In some embodiments, the heating device further includes a heater controller responsive to an input signal representative of a desired temperature $T_D$, to heat the heater element to the desired temperature $T_D$, the heater controller being coupled to the first and second wires, and adapted for application of a current therethrough, the current when passing through the heater element, effecting resistive losses therein to cause the heater element to be at a temperature T. In some embodiments, the heater controller is responsive in a closed loop to a detected resistance of the heater element between the two wires to adjustably control the current whereby the temperature T substantially equals $T_D$ over the operating range. In some embodiments, the heater controller includes a bridge circuit with the heater element forming an arm in the bridge circuit.

In some embodiments, the first and second grooves each receive a respective one of the first and second wires at least partially therewithin.

In some embodiments, each of the first and second wires is positioned orthogonal and adjacent to a respective one of the first and second grooves, along a side of the substrate opposite the heater element.

In some embodiments, the electrical interface is configured such that current flowing between the heater element and the first and second wires is confined to a path along the outside surfaces of the substrate.

In some embodiments, each of the first and second wires are positioned orthogonal and adjacent to a respective one of the first and second grooves, along a side of the substrate opposite the heater element, said wires expending in a direction at least in part orthogonal to the substrate axis.

In some embodiments, each of the first and second wires are positioned adjacent a respective end of the substrate, along a side of the substrate opposite the heater element. Some embodiments further include conductive material on the surface of the substrate extending from regions adjacent each of the first and second wires to the first and second conductive layers, respectively. The conductive material electrically couples each of the first and second wires to the first and second conductive layers, respectively.

In some embodiments, the substrate includes a ceramic material or a polyimide material.

In another aspect, disclosed is an apparatus for welding sutures which includes a first heater device and a second heater device, each of the heater devices adapted to simultaneously generate heat and sense temperature. During a welding operation, the first and second heater devices operate alternatively at repetitive intervals such that during every other interval the first heater is turned while the second heater is turned off, and during each respective succeeding interval the second heater is turned on while the first heater is turned off.

In some embodiments, at least one of the first and second heater devices includes a heater device of the type described above. In some embodiments, each of the repetitive intervals is an interval of about 20 milliseconds. In some embodiments, during a welding operation, the first and second heater devices operate alternatively at repetitive intervals of about 20 milliseconds for a total of less than 10 seconds.

Various embodiments may include any of the above described features, alone or in combination.

DETAILED DESCRIPTION

Figure 1:
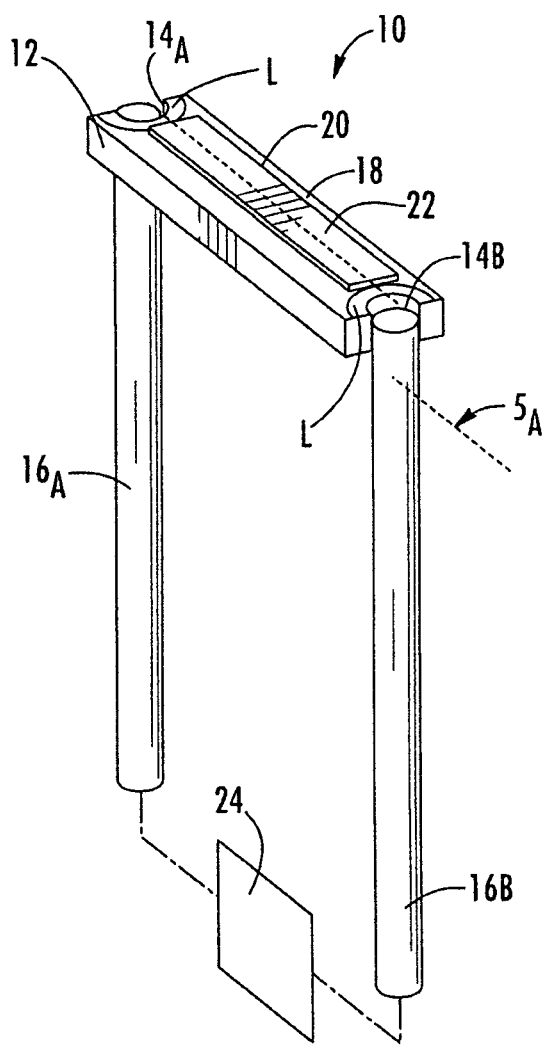
FIG. 1 is a schematic view of an exemplary heater device.

As shown in FIG. 1, an exemplary heater device 10 preferably includes a substrate 12 that extends along substrate axis $S_A$ of a predetermined and desired length and width. The specific dimensions of the substrate may be selected based on the dimensions of a thermal suture welding device with which the heater device 10 may be used. In typical embodiments, the dimensions are in the range suitable for use with an endoscopic surgical device.

The substrate 12 may be manufactured from any substantially non-conductive materials, such as a non-conductive ceramic or a polyimide. The substrate 12 is formed into a predetermined shape and size, and includes concave grooves 14A, 14B at the respective ends of the substrate 12 along the substrate axis $S_A$. Concave grooves 14A and 14B extend orthogonal to the substrate axis $S_A$. The grooves 14A, 14B preferably are shaped to receive wires 16A, 16B, respectively, at least partially therewithin. Preferably, the size and shape of the concave recesses 14A, 14B are shaped such that a wire 16A, 16B positioned therein is securely coupled against the walls therein.

As shown in FIG. 1, the surface of the substrate 12 preferably is planar to receive a joinder layer 20 thereupon, thus forming a heater support surface 18. In some embodiments, the heater support surface 18 is concave shaped to be positioned against a convex receiving surface to be welded or heated. In yet another embodiment, the support surface 18 may be convex, as may be required for a specific use.

As shown in FIG. 1, an electrically conductive joinder layer 20 is disposed on the heater support surface 18. In one embodiment, the joinder layer 20 is a layer of a tungsten alloy, such as titanium tungsten, having a thickness of 300-500 Angstroms. In this embodiment, the joinder layer 20 is applied using thin film fabrication technology, such as sputter deposition. Such sputter application of the joinder layer 20 creates a primarily mechanical bond between the joinder layer 20 and the adjacent heater support surface 18. Electrically conductive layers L extend from each of grooves 14A and 14B to a respective end of the heater 22. The electrically conductive layer extends at least partially into the recesses 14A, 14B. Next, the heater element 22, which may be in the form of a layer of conductive material, such as a metallic element, is applied using deposition technology. In this embodiment of heater 22, the layer or element is gold with thickness in the range of 200-3000 Angstroms thick, preferably about 2500 Angstroms thick, and also forms a primarily mechanical bond between the heater 22 and the joinder layer 20.

In an alternative embodiment, the joinder layer 18 may be disposed on the heater support surface 18 surface using a thick film technology. In this embodiment, the joinder layer 20 is disposed on the substrate by mixing conductive materials, such as a metal, with a joinder material. This mixture then is applied on the heater support surface 18. The conductive materials may include any conductive, elemental metal materials, including without limitation gold, silver, and titanium. The joinder materials may include epoxy, and polyimide, or any other material that can be mixed with the conductive metals and mechanically or otherwise applied securely on the joinder layer 20. The mixture of elemental metal materials and joinder material is applied mechanically to the joinder layer 20, such as by spraying, brushing, and drip coating. This joinder material is cured using an appropriate curing methodology as is well known to those skilled in the art. In an embodiment, the joinder material is heat cured at a time and temperature determined by the components of the joinder material, and as known to those skilled in the relevant art. In this embodiment, the heater element 22 is the same as the joinder layer 20 due to the presence of the metallic (conductive) material combined with a resistive (epoxy) material.

An aspect of the heater device 10 is that the electrically conductive layers L extend into the grooves 14A, 14B a sufficient distance to allow for an electrical wire 16A, 16B to make contact with that layer. In one embodiment, and as shown in FIG. 1, the wires 16A, 16B are positioned within the grooves 14A, 14B in such a manner as to create, at least in part, an interference fit. Alternatively, or in addition to the interference fit the wires 16A, 16B may be held in place within the grooves 14A, 14B by means of a thermal compression weld. It is preferable that the contact between the wires and joinder layer be a solderless contact to avoid any disruption to current flow and to increase the reliability of the contact between the wires and the joinder layer.

Figure 2:
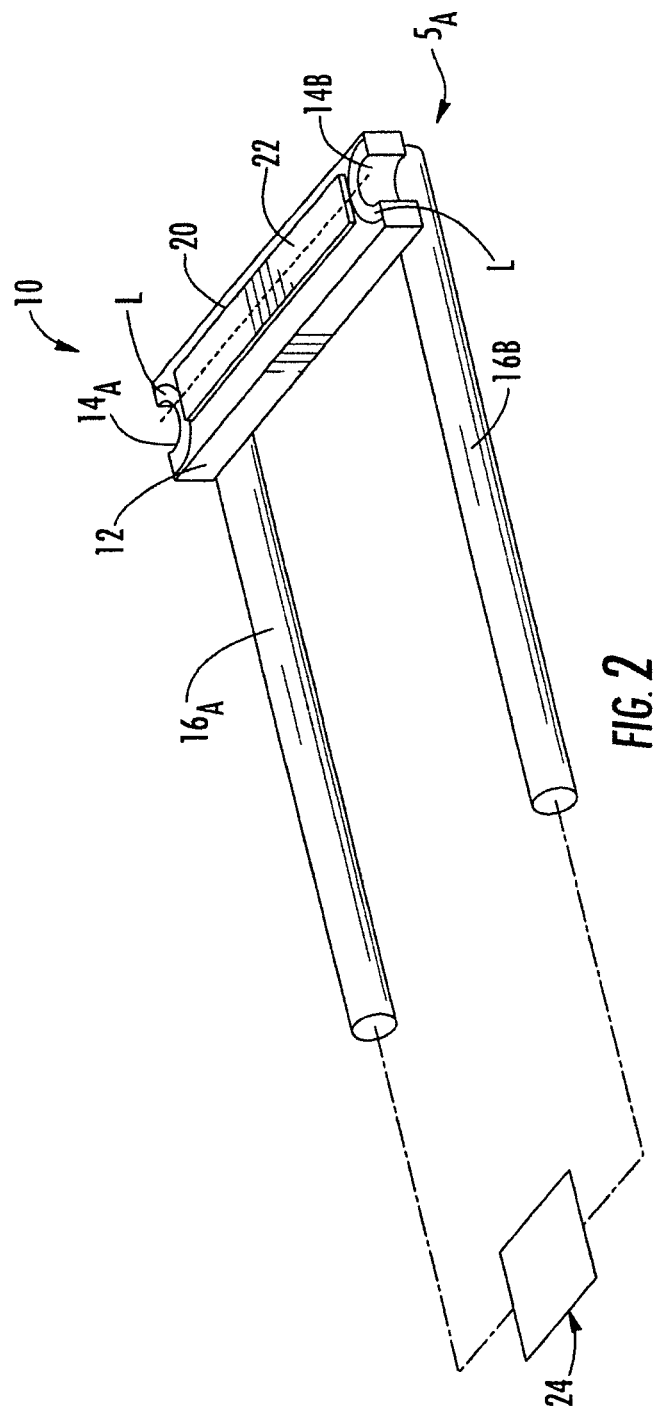
FIG. 2 is a schematic view of an alternative embodiment of the heater device.

In an alternative embodiment, as shown in FIG. 2, the electrical wires 16A, 16B are positioned orthogonal and adjacent to the grooves 14A, 15B, along the side of the substrate 12 opposite the heater 22. In this embodiment, the electrically conductive layers L extend completely through, or are integral with the grooves 14A, 14B so that electrical contact is made between the electrically conductive layers L and the wires 16A, 16B.

Figure 3:
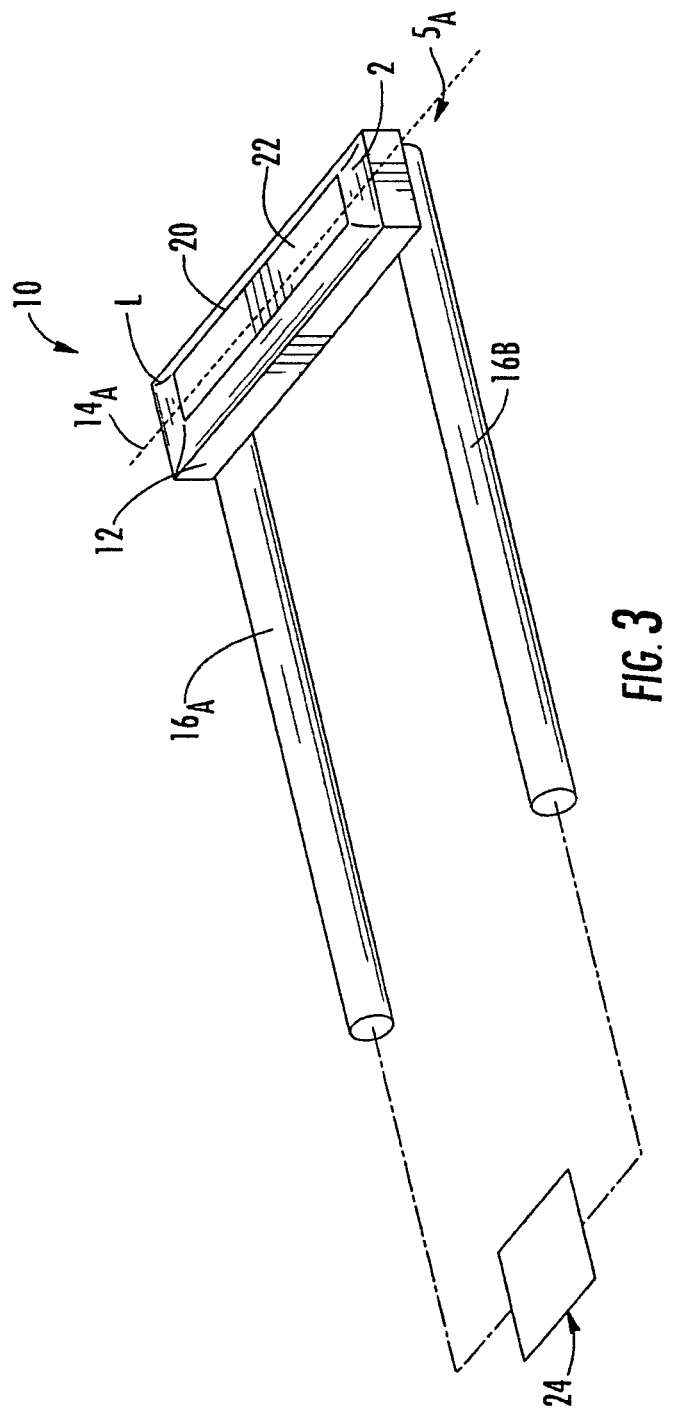
FIG. 3 is a schematic view of an alternative embodiment of the heater device.

In an alternate embodiment, and as shown in FIG. 3, the substrate 12 does not include grooves. Two wires 16A, 16B are positioned along the bottom side of the substrate 12, and substantially orthogonal to the substrate axis $S_A$. As in the embodiment of FIG. 2, the electrically conductive layers L extend along the ends of the substrate or are integral with the substrate in such a manner as to enable electrical contact between the wires 16A, 16B and electrically conductive layers L.

In yet another embodiment, the grooves 14A, 14B may be coated with an electrically conductive material, such a metallic material, that enables electrical current to pass from the electrical wires 16A, 16B, through such metallic material and to the electrically conductive layers L.

In the embodiment of FIG. 3, the metallic material may be located adjacent the wires 16A, 16B and extending either through the substrate or along a portion of the substrate from the wires to the electrically conductive layers L. In this embodiment, the electrical wires 16A, 16B may be bonded to the electrically conductive layers L or the metallic material in a solderless bond.

Note that, in some embodiments such as that shown in FIG. 3, the current passing from the wires 16A, 16B, through heater 22 may travel along a path limited to the outer surfaces of substrate 12, and not through the substrate 12.

As illustrated, the heater element 22 preferably is coupled to the joinder layer 20 such that the heater element axis $H_A$ is parallel with the substrate axis $S_A$. The heater element 22 includes an electrical contact at least at each end of the heater element 22 along its axis $H_A$, such that current can pass from the electrically conductive layers L through the heater element 22. Preferably, the heater element 22 is a resistive temperature device (RTD) having resistivity which varies monotonically with temperature over a predetermined temperature range or operating range. The heater element 22 may be coupled to the joinder layer 20 using a chemical, molecular, or mechanical bond, other bonding means generally available in the art.

The current coming in through the wires 16A, 16B may be varied by used of a heater controller 24 attached to one end of each wire 16A, 16B. In some embodiments, the heater controller 24 is responsive to an input signal representative of a desired temperature $T_D$ set by a user. In that embodiment, the heater controller 24 applies a voltage across wires 16A, 16B, driving a current through the heater 22. When the predetermined current passes through the heater element 22, it effects resistive losses in the heater element 22 causing the heater to reach a temperature T. Preferably the heater controller 24 is responsive, in a closed loop manner to detected resistance of the heater element 24, to adjustably control the current and maintain the heater element temperature T substantially at the same temperature as $T_D$ set by a user. In this manner, the user can set a desired temperature which is optimal for surgical suture welding, and according to the particular materials used in such welding. The heater controller 24 preferably includes a bridge circuit with the heater element 22 forming an arm in the bridge circuit. In alternative embodiments, temperature $T_D$ may be a constant or may vary over time.

In various embodiments, at least a portion of the path of current traveling through the wires and the heater may be covered in a dielectric coating, using suitable methods known in the art.

Figures 4A, 4B:
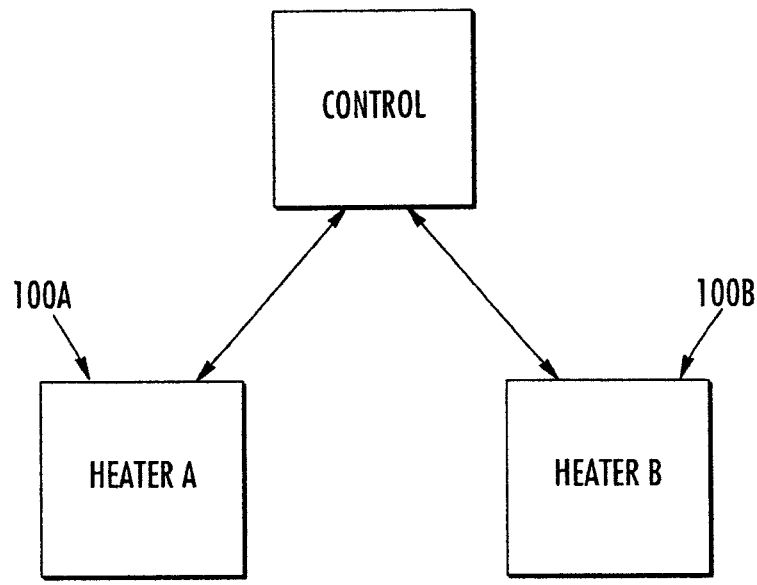
FIG. 4a is a block diagram of a suture welding apparatus featuring two heater devices.
FIG. 4b illustrates the switching of the heater devices shown in FIG. 4b Like reference numerals refer to like elements throughout the figures.

As shown in FIG. 4a, in one embodiments two heaters 100A, 100B are used to effect thermal welding. Each heater 100A, 100B may be of the types described above. In some embodiments, each heater 100A, 100B may simultaneously generate heat and sense temperature. The heaters 100A, 100B are operated alternately (e.g. as controlled by control unit 110), where each is, for example on for 20 milliseconds and off for 20 milliseconds respectively, for a total operation over a period of, in typical applications, up to about 10 seconds, e.g., a 3 second period. FIG. 4b illustrates this alternate operation of two heaters ("heater A" and heater B"), which are switched on and off during alternate repetitive intervals $t_1 \ldots t_n$. In further embodiments, more than two heaters may be used. The heaters may operate sequentially, or in any other suitable pattern to effect thermal welding.

One or more or any part thereof of techniques described above (e.g. temperature sensing/control) can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

The disclosure may be embodied in other specific forms without departing from the spirit or essential characteristics thereof. The present embodiments are therefore to be considered in all respects as illustrative and not restrictive, the scope of the disclosure being indicated by the appended claims rather than by the foregoing description. All changes that come within the meaning and range of the equivalency of the claims are therefore intended to be embraced therein.

The invention claimed is:

1. A heater device for thermally welding suture strands, comprising:
   A. a non-conductive substrate extending from a first end to a second end and being elongated along a substrate axis, and having a substantially planar heater support surface;
   B. an electrically conductive joinder layer disposed on said heater support surface;

C. an electrically conductive heater element extending from a first end to a second end and being elongated along a heater axis thereof and disposed on said joinder layer, said heater element being a layer and being coupled to said support surface by said joinder layer;

D. an electrical interface including a first electrically conductive element coupled to said first end of said heater element, and a second electrically conductive element coupled to said second end of said heater element wherein said electrical interface includes:
 i. a first wire extending from said first end of said substrate; and
 ii. a second wire extending from said second end of said substrate, and
 iii. a first electrically conductive layer disposed on said substrate and said joinder layer, and electrically coupling said first wire and said first end of said heater element, and
 iv. a second electrically conductive layer disposed on said substrate and said joinder layer, and electrically coupling said second wire and said second end of said heater element.

2. A heater device according to claim 1, wherein said substrate includes:
 a first open-faced groove in said first end thereof and extending from and at least in part orthogonal to said support layer, and
 a second open-faced groove in said second end thereof and extending from and at least in part orthogonal to said support layer,
 wherein said first groove and said second groove each include a metal layer disposed at least in part thereon, and wherein said first wire and said second wire are bonded to a respective one of said metal layers of said first groove and said second groove.

3. A heater device according to claim 2, wherein each of the first and second wires extend from respective ends of the substrate in a direction at least in part orthogonal to said support surface.

4. A heating device according to claim 1 wherein said heater element layer has a thickness in the range 2000-3000 Angstroms.

5. A heating device according to claim 1, wherein said heater element is gold.

6. A heating device according to claim 1, wherein said joinder layer has a thickness in the range 300-500 Angstroms.

7. A heating device according to claim 6, wherein said joinder layer is a tungsten alloy.

8. A heating device according to claim 2, wherein said metal layers are gold.

9. A heating device according to claim 8, wherein said metal layers have a thickness in the range of 900-1100 Angstroms.

10. A heater device according to claim 2, wherein said bonding between said first and second wires to said metal layers of said grooves is solderless.

11. A heater device according to claim 10, wherein said bonding is at least in part a thermal compression weld.

12. A heater device according to claim 10, wherein said grooves have a partial conical contour and said bonding is at least in part an interference fit.

13. A heater device according to claim 1, wherein said heater element is a resistive temperature device (RTD) having resistivity which varies monotonically with temperature over a predetermined operating temperature range.

14. A heater device according to claim 13, further comprising a heater controller responsive to an input signal representative of a desired temperature TD, to heat said heater element to said desired temperature TD, said heater controller being coupled to said first and second wires, and adapted for application of a current therethrough, said current when passing through said heater element, effecting resistive losses therein to cause said heater element to be at a temperature T.

15. A heater according to claim 14, wherein said heater controller is responsive in a closed loop to a detected resistance of said heater element between said two wires to adjustably control said current whereby said temperature T substantially equals TD over said operating range.

16. A heater device according to claim 15, wherein said heater controller includes a bridge circuit with said heater element forming an arm in said bridge circuit.

17. A heater device according to claim 3, wherein the first and second grooves each receive a respective one of the first and second wires at least partially therewithin.

18. A heater device according to claim 2, wherein each of the first and second wires are positioned orthogonal and adjacent to a respective one of the first and second grooves, along a side of the substrate opposite the heater element, said wires expending in a direction at least in part orthogonal to the substrate axis.

19. A heater device according to claim 1, wherein each of the first and second wires is positioned adjacent a respective end of the substrate, along a side of the substrate opposite the heater element.

20. A heather device of claim 19 further comprising conductive material on the surface of the substrate extending from regions adjacent each of the first and second wires to the first and second conductive layers, respectively, wherein said conductive material electrically couples each of the first and second wires to the first and second conductive layers, respectively.

21. A heater device according to claim 1, wherein the electrical interface is configured such that, during operation, current flowing between the heater element and the first and second wires is confined to a path along the outside surfaces of the substrate.

22. A heater device according to claim 1, wherein the substrate comprises a ceramic material or a polyimide material.

23. An apparatus for welding sutures comprising:
 a first heater device s set forth in claim 1 and a second heater device, each of said heater devices adapted to simultaneously generate heat and sense temperature;
 wherein, during a welding operation, the first and second heater devices operate alternatively at repetitive intervals such that during every other interval the first heater is turned while the second heater is turned off, and during each respective succeeding interval the second heater is turned on while the first heater is turned off.

24. The apparatus of claim 23, wherein the second heater device comprises:
 A. a substrate extending from a first end to a second end along a substrate axis, and having a substantially planar heater support surface;
 B. a joinder layer disposed on said heater support surface;
 C. a heater element extending from a first end to a second end along a heater axis thereof and disposed on said joinder layer, said heater element being a layer and being coupled to said support surface by said joinder layer;
 D. an electrical interface including a first electrically conductive element coupled to said first end of said heater element, and a second electrically conductive element coupled to said second end of said heater element.

25. The device of claim 24, wherein each of the repetitive intervals is an interval of about 20 milliseconds.

26. The device of claim 25, wherein, during a welding operation, the first and second heater devices operate alternatively at repetitive intervals for a total period of less than about 10 seconds.

* * * * *